US007011855B2

(12) United States Patent
Martis et al.

(10) Patent No.: US 7,011,855 B2
(45) Date of Patent: Mar. 14, 2006

(54) BIOCHEMICALLY BALANCED PERITONEAL DIALYSIS SOLUTIONS

(75) Inventors: Leo Martis, Long Grove, IL (US); Lee W. Henderson, Lake Forest, IL (US)

(73) Assignee: Baxter International Inc., Deerfield, IL (US)

( * ) Notice: Subject to any disclaimer, the term of this patent is extended or adjusted under 35 U.S.C. 154(b) by 344 days.

(21) Appl. No.: 09/955,248

(22) Filed: Sep. 17, 2001

(65) Prior Publication Data

US 2002/0037329 A1 Mar. 28, 2002

Related U.S. Application Data

(63) Continuation of application No. 08/421,020, filed on Apr. 12, 1995, which is a continuation of application No. 08/269,497, filed on Jul. 1, 1994, now abandoned.

(51) Int. Cl.
*A61K 33/00* (2006.01)
*A61K 31/70* (2006.01)
*A61K 31/19* (2006.01)

(52) U.S. Cl. ............... 424/717; 424/665; 424/680; 424/682; 424/700; 424/722; 514/557; 514/578; 210/645; 604/29

(58) Field of Classification Search ............... 514/557, 514/578; 210/645; 604/29; 424/665, 680, 424/682, 700, 717, 722

See application file for complete search history.

(56) References Cited

U.S. PATENT DOCUMENTS

| | | |
|---|---|---|
| 4,396,383 A | 8/1983 | Hart |
| 4,465,488 A | 8/1984 | Richmond et al. |
| 4,489,535 A | 12/1984 | Veltman |
| 4,584,176 A | 4/1986 | Oliver et al. |
| 4,630,727 A | 12/1986 | Feriani et al. |
| 4,663,166 A * | 5/1987 | Veech ............... 424/663 |
| 4,756,838 A | 7/1988 | Veltman |
| 4,863,714 A | 9/1989 | Sovak et al. |
| 4,879,280 A | 11/1989 | Seyffart et al. |
| 4,959,175 A | 9/1990 | Yatzidis |
| 5,039,609 A | 8/1991 | Klein |
| 5,100,677 A * | 3/1992 | Veech ............... 424/677 |
| 5,141,492 A | 8/1992 | Dadson et al. |
| 5,211,643 A | 5/1993 | Reinhardt et al. |
| 5,296,242 A * | 3/1994 | Zander ............... 424/715 |
| 5,383,324 A | 1/1995 | Segers et al. |
| 5,423,421 A | 6/1995 | Inoue et al. |
| 5,431,496 A | 7/1995 | Balteau et al. |
| 5,462,526 A | 10/1995 | Barney et al. |
| 5,509,898 A | 4/1996 | Isono et al. |
| 5,536,469 A | 7/1996 | Jonsson et al. |
| 5,560,403 A | 10/1996 | Balteau et al. |
| 5,610,170 A | 3/1997 | Inoue et al. |
| 5,706,937 A | 1/1998 | Futagawa et al. |
| 5,853,388 A | 12/1998 | Semel |
| 5,871,477 A | 2/1999 | Isono et al. |
| 5,945,129 A | 8/1999 | Knerr et al. |
| 6,020,007 A * | 2/2000 | Veech ............... 424/677 |

FOREIGN PATENT DOCUMENTS

| | | |
|---|---|---|
| DE | 19748290 | 5/1999 |
| EP | 0 083 360 | 10/1981 |
| EP | 0 165 933 B1 | 2/1986 |
| EP | 0 249 667 B1 | 12/1987 |
| EP | 0 278 100 | 6/1988 |
| EP | 0 277 868 | 10/1988 |
| EP | 0 209 607 | 12/1989 |
| EP | 0 399 549 | 11/1990 |
| EP | 0 439 061 B1 | 7/1991 |
| EP | 0613688 | 9/1994 |
| EP | 0 647 145 B1 | 4/1995 |
| EP | 0 776 649 A2 | 6/1997 |
| EP | 0935967 | 3/1998 |
| EP | 0 845 970 | 1/2000 |
| FR | 2753099 | 3/1998 |
| JP | 56164113 | 12/1981 |
| JP | 2304026 | 12/1990 |
| JP | 3195561 | 8/1991 |
| JP | 5105633 | 4/1993 |
| JP | 6105905 | 4/1994 |
| JP | 7252137 | 10/1995 |
| JP | 8131542 | 5/1996 |
| JP | 8164199 | 6/1996 |
| JP | 9087182 | 3/1997 |
| JP | 9110703 | 4/1997 |
| JP | 9301875 | 11/1997 |

(Continued)

OTHER PUBLICATIONS

Schambye et al., *The Cytotoxicity of Continuous Ambulatory Peritoneal Dialysis Solutions with Different Bicarbonate/ Lactate Ratios*, Peritoneal Dialysis International, vol. 13, Suppl. 2, Oct. 1-4, 1992, pp. S116-S118.

American Society for Artificial Internal Organs, 1994 Abstracts.

Boen ST, *A Clinical Study of Factors Governing its Effectiveness*, Peritoneal Dialysis, p. 76, Van Gorcum & Co., Assen, The Netherlands (1959).

(Continued)

*Primary Examiner*—Rosalynd Keys
(74) *Attorney, Agent, or Firm*—Paula J. F. Kelly; Robert Barrett

(57) ABSTRACT

A peritoneal dialysis solution that is biochemically balanced to correct metabolic acidosis associated with chronic renal failure in a more physiological manner. The peritoneal dialysis solution has a physiological pH, e.g., pH of 7.0 to 7.4, and contains bicarbonate at a concentration that is found in normal blood. Additionally, the solution contains carbon dioxide at a partial pressure that is similar to partial pressure of carbon dioxide found in normal blood. The peritoneal dialysis solution also contains a weak acid with a pKa of less than 5.0.

15 Claims, No Drawings

FOREIGN PATENT DOCUMENTS

| | | |
|---|---|---|
| JP | 10201821 | 8/1998 |
| JP | 11-9659 | 1/1999 |
| JP | 11004872 | 1/1999 |
| JP | 11019178 | 1/1999 |
| WO | WO 86/03407 | 6/1986 |
| WO | WO 87/03809 | 7/1987 |
| WO | WO 91/18610 | 12/1991 |
| WO | WO 95/19778 | 7/1995 |
| WO | WO 96/01118 | 1/1996 |
| WO | WO 97/05851 | 2/1997 |
| WO | 98/10733 | 3/1998 |
| WO | 99/01144 | 1/1999 |
| WO | 99/09953 | 3/1999 |
| WO | 99/09953 | 4/1999 |
| WO | 99/22746 | 5/1999 |
| WO | 99/27885 | 6/1999 |

OTHER PUBLICATIONS

Faller et al., "Loss of Ultrafiltration in Continuous Ambulatory Peritoneal Dialysis: A Role for Acetate", Peritoneal Dialysis Bulletin, Jan.-Mar. 1984, pp. 10-13.

Feriani et al., *Bicarbonate Solutions for Peritoneal Dialysis: A Reality*, Int J ARtif Organs 8:57-58 (1985).

Ing et al., *Preparation of Bicarbonate-Containing Dialysate for Peritoneal Dialysis*, Int J Artif Organs, vol. 6, No. 4, pp. 217-218 (1983).

*The Merck Index*, 12$^{th}$ Ed., Merck Research Laboratories, Whitehouse Station, NJ, p. 1472 (1996).

Murphey et al., *Use of an ARtificial Kidney*, J. Lab. Clin. Med., vol. 40, pp. 436-444 (1952).

Odel HM et al., Peritoneal Lavage as an Effective Means of Extrarenal Excretion. A Clinical Appraisal, American Journal of Medicine, vol. 9, 63-88 (1950).

Schambye et al., *The Cytotoxicity of Continuous Ambulatory Peritoneal Dialisis Solutions with Different Bicarbonate/Lactate Ratios*, Peritoneal Dialysis International, vol. 13, Suppl. 2, Oct. 1-4, 1992, pp. S116-S118.

Simonsen et al., Less Infusion Pain and Elevated Level of Cancer Antigen 125 by the Use of a New and More Biocompatible PD Fluid, Advances in Peritoneal Dialysis, vol. 12, pp. 156-160 (1996).

T.S. Ing. et al., Bicarbonate-Buffered Peritoneal Dialysis, The International Journal of Artificial Organs, vol. 8, no. 3, p. 121-124 (1985).

* cited by examiner

BIOCHEMICALLY BALANCED PERITONEAL DIALYSIS SOLUTIONS

This is a continuation of U.S. patent application Ser. No. 08/421,020, filed on Apr. 12, 1995, which is a continuation of U.S. patent application Ser. No. 08/269,497, filed on Jul. 1, 1994 abandonded.

BACKGROUND OF THE INVENTION

The present invention relates generally to peritoneal dialysis. More specifically, the present invention relates to peritoneal dialysis solutions.

It is known to use dialysis to support a patient whose renal function has decreased to the point where the kidneys no longer sufficiently function. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semi-permeable membrane. The peritoneum is the membranous lining of the abdominal cavity that due to a large number of blood vessels and capillaries is capable of acting as a natural semi-permeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows the proper acid-base of electrolytes and fluid balance to be returned to the blood and the dialysis solution is simply drained from the body cavity through the catheter.

A number of dialysis solutions have been utilized and suggested. One of the difficulties with dialysis solutions that are used for peritoneal dialysis is that they are not ideal solutions for maintaining acid base homeostasis. Metabolic acidosis is a catabolic event that can occur in peritoneal dialysis patients.

In this regard, the kidneys play a major role in the maintenance of the acid-base balance. In chronic renal failure, the acid generated from the metabolism of dietary proteins can lead to metabolic acidosis. Metabolic acidosis can have a profound and acute effect on the respiratory, cardiac, and/or nervous systems. Long term consequences of metabolic acidosis include protein malnutrition and skeletal diseases.

Lactate has been utilized in peritoneal dialysis solutions for the purpose of maintaining acid-base balance in peritoneal dialysis patients. Typical commercially available peritoneal dialysis solutions contain 35 to 40 mEq/L of lactate.

These solutions are adequate in maintaining acid-base balance in a number of dialysis patients. However, patients who are deficient in lactate metabolism and/or who also experience or suffer from hepatic failure or shock can develop lactic acidosis. This syndrome includes as characteristic symptoms hyperventilation, abdominal pain, and disturbances in consciousness while the patient receives lactate-containing peritoneal dialysis fluids.

An additional issue with respect to lactate peritoneal dialysis solutions is that a number of in vitro studies performed with peritoneal cells indicate that altered cell function can occur when peritoneal cells are exposed to large concentrations of lactate. These changes in cell function can compromise host defense leading to increased rates of infection and damage to the peritoneal membrane.

In order to address this issue, peritoneal dialysis solutions in which lactate is completely replaced by bicarbonate have been proposed. However, in order to balance total body hydrogen ion content against metabolically generated hydrogen, and to maintain normal plasma carbonic acid and bicarbonate concentrations, it is necessary to use bicarbonate concentrations that are considerably in excess of normal. In this regard, bicarbonate concentration upwards of 38 mM/L are believed to be necessary.

Because it is necessary to maintain the solution at a physiological pH, the requirement of such a high bicarbonate solution requires a partial pressure of carbon dioxide ($pCO_2$) that is at least twice the physiologic $pCO_2$ (e.g., greater than 80 mmHg). Although such a solution may meet the metabolic needs of the patient, such a solution does not provide a physiological environment for the peritoneal cells in contact with the solution. Due to the differences in transport rates between bicarbonate and carbon dioxide, with such a solution, the intracellular hydrogen ion concentration of the cell's lining the peritoneal cavity, as well as those present in the peritoneal cavity, would be severely low placing them at a metabolic disadvantage. This metabolic disadvantage will increase more than would be expected if they share the extracellular environment of normal pH, but a supernormal bicarbonate and $pCO_2$.

There is therefore a need for a peritoneal dialysis solution that adequately addresses the problem of metabolic acidosis associated with end stage renal disease.

SUMMARY OF THE INVENTION

The present invention provides a peritoneal dialysis solution that is biochemically balanced to correct metabolic acidosis associated with chronic renal failure in a more physiological manner. The peritoneal dialysis solution has a physiological pH, e.g., pH of 7.0 to 7.4, and contains bicarbonate at a concentration that is found in blood involved in diffusive transport of solutes with dialysis fluid. This will block the loss of bicarbonate during peritoneal dialysis which is the case with present solutions. Additionally, the solution contains carbon dioxide at a partial pressure that is similar to partial pressure of carbon dioxide found in the blood capillaries. The peritoneal dialysis solution also contains a weak acid with a pKa of less than 5.0 at an amount needed to neutralize acid generated from endogenous metabolism. These weak acids are also the normal biochemical intermediates of glucose metabolism resulting in neutral end products.

To this end, the present invention provides a peritoneal dialysis solution including bicarbonate at a level of less than or equal to 30 mM/L, having a $pCO_2$ that is less than 60 mmHg, and including at least one weak acid selected from the group consisting of: lactate; pyruvate; citrate; isocitrate; cis-aconitase; α-ketoglutarate; succinate; fumarate; malate; and oxaloacetate.

In an embodiment of the peritoneal dialysis solution, bicarbonate is present in the solution at 25 mM/L.

In an embodiment of the peritoneal dialysis solution, the weak acid is present in an amount comprising approximately 10 mEq/L to about 20 mEq/L.

In an embodiment of the peritoneal dialysis solution, the $pCO_2$ of the solution is approximately the same as the $pCO_2$ of blood.

In an embodiment of the peritoneal dialysis solution, the solution has a pH of approximately 7.4.

In an embodiment of the peritoneal dialysis solution, the weak acids have a pKa of <5.0.

In another embodiment, the present invention provides a peritoneal dialysis solution comprising:

| | |
|---|---|
| Dextrose (hydrous) (g/dl) | 1.5–4.25 |
| Sodium (mEq/L) | 100–140 |
| Chloride (mEq/L) | 70–110 |
| Calcium (mEq/L) | 0.0–4.0 |
| Magnesium (mEq/L) | 0.0–4.0 |
| Bicarbonate (mEq/L) | 20.0–30.0 |
| Weak acid (mEq/L) | 10.0–20.0 | wherein the weak acid is chosen from the group consisting of: lactate; pyruvate; citrate; isocitrate; cisaconitase; α-ketoglutarate; succinate; fumarate; malate; and oxaloacetate.

In an embodiment, the solution includes an osmotic agent other than dextrose.

In an embodiment, the present invention provides a method for correcting metabolic acidosis in a dialysis patient suffering or likely to suffer from same comprising the step of administering to a dialysis patient a peritoneal dialysis solution that has a bicarbonate level and carbon dioxide partial pressure that is substantially similar to that found in the normal person's blood.

An advantage of the present invention is that it provides an improved peritoneal dialysis solution.

Another advantage of the present invention is that it provides bicarbonate to the patient when blood bicarbonate is below normal.

Still an advantage of the present invention is that it removes bicarbonate when blood bicarbonate is above normal.

Another advantage of the present invention is that it provides a biochemically balanced peritoneal dialysis solution.

Furthermore, an advantage of the present invention is that it provides a peritoneal dialysis solution that corrects metabolic acidosis associated with end stage renal disease.

Moreover, an advantage of the present invention is that it provides a peritoneal dialysis solution that balances bicarbonate at a normal concentration with a $pCO_2$ at normal partial pressure.

Further, an advantage of the present invention is that the dialysis solution provides an additional contribution of bicarbonate by diffusion of bicarbonate to offset the end balance of the metabolic hydrogen load and vice versa for a supernormal concentration.

Another advantage of the present invention is that it provides a peritoneal dialysis solution at a physiological pH.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides improved peritoneal dialysis solutions. The solutions are biochemically balanced to correct metabolic acidosis that is associated with chronic renal failure. Pursuant to the present invention, the solutions are biochemically balanced in a more physiological manner than prior peritoneal solutions.

To this end, the present invention provides peritoneal dialysis solutions that contain bicarbonate at a more physiological level, e.g., at a level substantially equivalent to that found in normal blood.

The peritoneal dialysis solution of the present invention, in an embodiment, includes bicarbonate present at a level of approximately 20 mM/L to about 30 mM/L. In a most preferred embodiment, bicarbonate is present at a level of 25 mM/L.

Additionally, the solution contains carbon dioxide at a partial pressure that is less than 60 mmHg. In a preferred embodiment the $pCO_2$ of the solution is similar to the partial pressure of carbon dioxide found in blood capillaries.

Further, preferably, the dialysis solutions have a pH of 7.4. Therefore, the solution, although balanced biochemically, is a physiologically acceptable solution.

Additionally, the solutions include a weak acid with a pKa of less than 5. These weak acids are chosen so as to be normal biochemical intermediates of glucose metabolism. Preferably, the weak acids are chosen from the group consisting of: lactate; pyruvate; citrate; isocitrate; cis-aconitase; α-ketoglutarate; succinate; fumarate; malate; and oxaloacetate. These acids can be present either alone or in combination in the solution. Preferably, the weak acids are present at a level of approximately 10 to about 20 mEq/L. Preferably, the weak acid are present mainly as sodium salts. The weak acid is present in an amount that would offset the daily metabolic hydrogen production of approximately 1 mEq/kg/day.

In an embodiment, the peritoneal dialysis solution used in the method for correcting metabolic acidosis does not include lactate.

Pursuant to the present invention, any osmotic agent can be used in the solution. For example, dextrose, maltodextrin, glycerol, polyglucose, polypeptides and amino acids can be used as the osmotic agent.

Preferably, the peritoneal dialysis solution, if it contains dextrose as an osmotic agent, has a general composition such as that set forth below:

| | |
|---|---|
| Dextrose (hydrous) (g/dl) | 1.5–4.25 |
| Sodium (mEq/L) | 100–140 |
| Chloride (mEq/L) | 70–110 |
| Calcium (mEq/L) | 0.0–4.0 |
| Magnesium (mEq/L) | 0.0–4.0 |
| Bicarbonate (mEq/L) | 20.0–30.0 |
| Weak acid (mEq/L) | 10.0–20.0 |
| pH | 7.0–7.4 |

Preferably, solutions containing an osmotic agent other than dextrose composition have the general composition:

| | |
|---|---|
| Osmotic agent (miy/L) | 1–200 |
| Sodium (mEq/L) | 100–140 |
| Chloride (mEq/L) | 70–110 |
| Calcium (mEq/L) | 0.0–4.0 |
| Magnesium (mEq/L) | 0.0–4.0 |
| Bicarbonate (mEq/L) | 20.0–30.0 |
| Weak Acid (mEq/L) | 10–20.00 |
| pH | 7.0–7.4 |

The peritoneal dialysis solutions of the present invention balance bicarbonate at normal concentrations and have a $pCO_2$ at normal partial pressure. The weak acid under usual circumstances will have an infinite gradient from dialysate to blood. Thus, the weak acid can be expected to perform in a relatively predictable manner in correcting the metabolic acidosis of chronic uremia.

Due to the composition of the present invention, should the patient's bicarbonate level drop below prescribed normal blood figure of 25 mM/L, then there will be an additional contribution by diffusion of bicarbonate to offset the unbalanced metabolic hydrogen load and vice versa for a supernormal concentration. Phrased in a different manner, the solution has a built in servo mechanism around the figure of 25 mM/L for bicarbonate. A pure bicarbonate solution at higher than normal concentrations does not offer this benefit.

By way of example, and not limitation, examples of specific peritoneal dialysis solutions of the present invention will now be given.

EXAMPLE NO. 1

| | |
|---|---|
| Dextrose (hydrous) (g/dl) | 1.5 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 25.00 |
| Lactate (mEq/L) | 15 |
| pH | 7.4 |

EXAMPLE NO. 2

| | |
|---|---|
| Dextrose (hydrous) (g/dl) | 2.5 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 25.00 |
| Lactate (mEq/L) | 15.0 |
| pH | 7.4 |

EXAMPLE NO. 3

| | |
|---|---|
| Dextrose (hydrous) (g/dl) | 4.25 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 25.00 |
| Lactate (mEq/L) | 15.0 |
| pH | 7.4 |

EXAMPLE NO. 4

| | |
|---|---|
| Dextrose (hydrous) (g/dl) | 1.5 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 20 |
| Lactate (mEq/L) | 20 |
| pH | 7.4 |

EXAMPLE NO. 5

| | |
|---|---|
| Dextrose (hydrous) (g/dl) | 2.25 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 20.0 |
| Lactate (mEq/L) | 20.0 |
| pH | 7.4 |

EXAMPLE NO. 6

| | |
|---|---|
| Dextrose (hydrous) (g/dl) | 4.25 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 20 |
| Lactate (mEq/L) | 20 |
| pH | 7.4 |

EXAMPLE NO. 7

| | |
|---|---|
| Dextrose (hydrous) (g/dl) | 1.5 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 30.0 |
| Lactate (mEq/L) | 10.0 |
| pH | 7.4 |

EXAMPLE NO. 8

| | |
|---|---|
| Dextrose (hydrous) (g/dl) | 2.50 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 30.0 |
| Lactate (mEq/L) | 10.0 |
| pH | 7.4 |

EXAMPLE NO. 9

| | |
|---|---|
| Dextrose (hydrous) (g/dl) | 4.25 |
| Sodium (mEq/L) | 132 |
| Chloride (mEq/L) | 96 |
| Calcium (mEq/L) | 3.5 |
| Magnesium (mEq/L) | 0.5 |
| Bicarbonate (mEq/L) | 30.0 |
| Lactate (mEq/L) | 10.0 |
| pH | 7.4 |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A peritoneal dialysis solution including bicarbonate at a level of less than or equal to 30 mM/L, having a carbon dioxide partial pressure that is less than 60 mmHg and including a weak acid at a level of between approximately 15 mEq/L and approximately 20 mEq/L selected from the group consisting of: lactate; citrate; isocitrate; cis-aconitase; α-ketoglutarate; succinate; fumarate; malate; and oxaloacetate.

2. The peritoneal dialysis solution of claim 1 wherein bicarbonate is present in the solution at 25 mM/L.

3. The peritoneal dialysis solution of claim 1 wherein the carbon dioxide partial pressure of the solution is approximately the same as the carbon dioxide partial pressure of blood.

4. The peritoneal dialysis solution of claim 1 wherein the solution has a pH of approximately 7.0 to about 7.4.

5. The peritoneal dialysis solution of claim 1 wherein the weak acids have a pKa of <5.0.

6. A peritoneal dialysis solution comprising:

| | |
|---|---|
| Dextrose (hydrous) (g/dl) | 1.5–4.25 |
| Sodium (mEq/L) | 100–140 |
| Chloride (mEq/L) | 70–110 |

-continued

| | |
|---|---|
| Calcium (mEq/L) | 0.0–4.0 |
| Magnesium (mEq/L) | 0.0–4.0 |
| Bicarbonate (mEq/L) | 20.0–30.0 |
| Weak acid (mEq/L) | 10.0–20.0 | wherein the weak acid is chosen from the group consisting of: lactate; citrate; isocitrate; cis-aconitase; α-ketoglutarate; succinate; fumarate; malate; and oxaloacetate, the solution having a carbon dioxide partial pressure that is less than 60 mmHg.

7. The peritoneal dialysis solution of claim 6 wherein the solution has a pH of approximately 7.0 to about 7.4.

8. The peritoneal dialysis solution of claim 6 wherein the weak acids have a pKa of <5.0.

9. The peritoneal dialysis solution of claim 6 wherein the carbon dioxide partial pressure of the solution is approximately the same as the carbon dioxide partial pressure of normal blood.

10. A peritoneal dialysis solution comprising:

| | |
|---|---|
| Dextrose (hydrous) (g/dl) | 1.5–4.25 |
| Sodium (mEq/L) | 100–140 |
| Chloride (mEq/L) | 70–110 |
| Calcium (mEq/L) | 0.0–4.0 |
| Magnesium (mEq/L) | 0.0–4.0 |
| Bicarbonate (mEq/L) | 20.0–30.0 |
| Weak acid (mEq/L) | 10.0–20.0 | wherein the weak acid is chosen from the group consisting of: lactate; citrate; isocitrate; cis-aconitase; α-ketoglutarate; succinate; fumarate; malate; and oxaloacetate, and the solution has a carbon dioxide partial pressure that is substantially similar to the carbon dioxide partial pressure of a normal subject's blood and the solution has a pH of approximately 7.0 to about 7.4.

11. A method for correcting metabolic acidosis in a dialysis patient suffering or likely to suffer from same comprising the step of:

administering to a patient a peritoneal dialysis solution that has a bicarbonate level and carbon dioxide partial pressure that are substantially similar to that found in the normal persons blood wherein the solution comprises:

| | |
|---|---|
| Dextrose (hydrous) (g/dl) | 1.5–4.25 |
| Sodium (mEq/L) | 100–140 |
| Chloride (mEq/L) | 70–110 |
| Calcium (mEq/L) | 0.0–4.0 |
| Magnesium (mEq/L) | 0.0–4.0 |
| Bicarbonate (mEq/L) | 20.0–30.0 |
| Weak acid (mEq/L) | 10.0–20.0 | wherein the weak acid is chosen from the group consisting of: lactate; citrate; isocitrate; cis-aconitase; α-ketoglutarate; succinate; fumarate; malate; and oxaloacetate.

12. The method of claim 11 including the step of administering to the patient a weak acid that is present in the solution in an amount that offsets the daily hydrogen production of approximately 1 mEq/kg/day.

13. The method of claim 12 wherein the weak acid have a pKa of <5.0.

14. The method of claim 11 wherein the solution has a pH of approximately 7.0 to about 7.4.

15. The method of claim 11 wherein the solution does not include lactate.

* * * * *